United States Patent
Andersson et al.

[11] Patent Number: 6,064,910
[45] Date of Patent: May 16, 2000

[54] RESPIRATOR RATE/RESPIRATION DEPTH DETECTOR AND DEVICE FOR MONITORING RESPIRATORY ACTIVITY EMPLOYING SAME

[75] Inventors: Jonas Andersson, Johanneshov; Johan Lidman, Stockholm; Carolina Bigert, Johanneshov, all of Sweden

[73] Assignee: Pacesetter AB, Järfälla, Sweden

[21] Appl. No.: 08/978,366

[22] Filed: Nov. 25, 1997

[30] Foreign Application Priority Data

Nov. 25, 1996 [SE] Sweden ................................. 9604320

[51] Int. Cl.[7] .......................... A61N 1/365; A61B 5/0205
[52] U.S. Cl. ................ 607/20; 607/22; 600/528; 600/529
[58] Field of Search .................... 600/528–542; 607/18, 20, 42

[56] References Cited

U.S. PATENT DOCUMENTS

| 4,981,139 | 1/1991 | Pfohl | 600/484 |
| 5,022,402 | 6/1991 | Schieberl et al. | 600/534 |
| 5,448,996 | 9/1995 | Bellin et al. | 600/574 |

*Primary Examiner*—Jeffrey R. Jastrzab
*Attorney, Agent, or Firm*—Hill & Simpson

[57] ABSTRACT

A device for determining the respiration rate and/or respiration depth of a patient includes a sensor for sensing heart sounds and an analyzer for analyzing the variation of the amplitude of the sensed heart sounds to determine the respiration rate and/or respiration depth from this amplitude variation. An apparatus for monitoring the respiration of a patient includes such a device and the analyzer is arranged to determine an anomaly in the amplitude variation of the sensed heart sounds as an indication of a respiration anomaly.

27 Claims, 3 Drawing Sheets

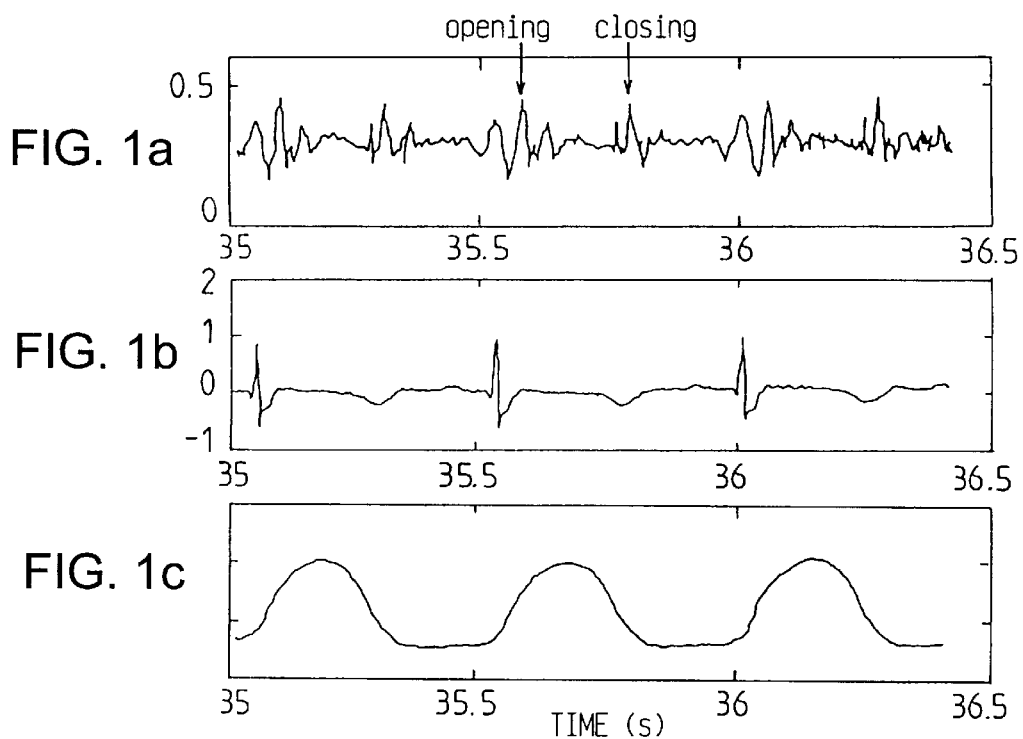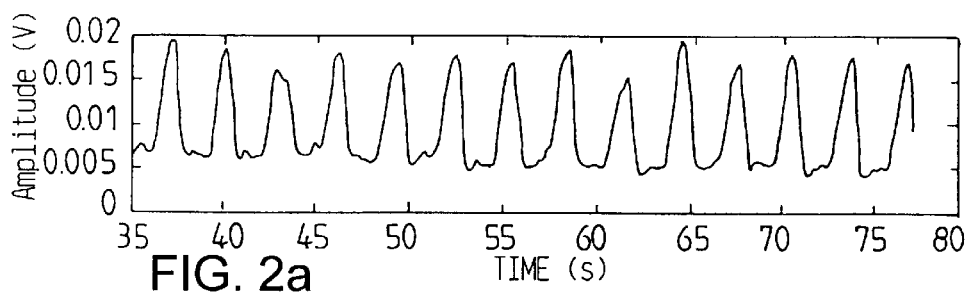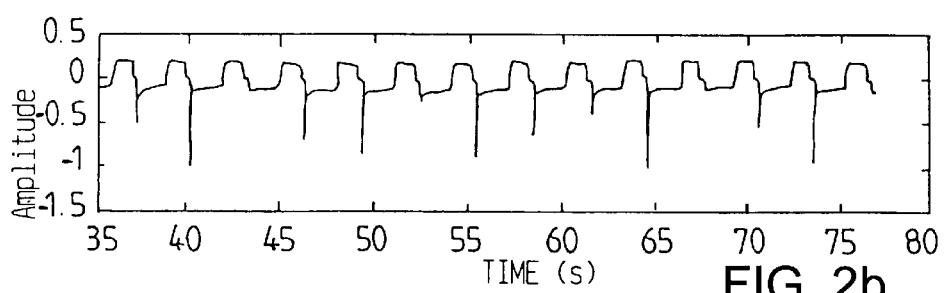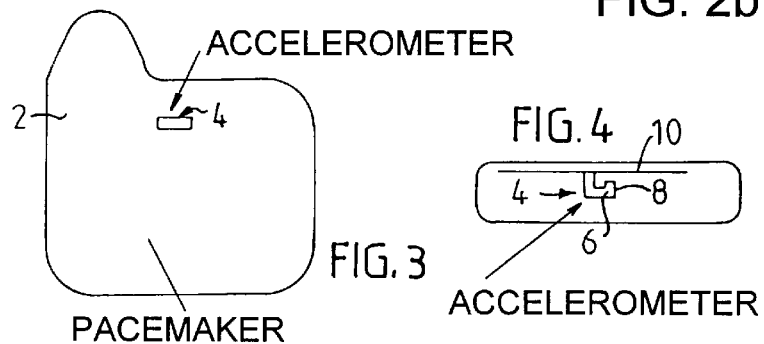

RESPIRATOR RATE/RESPIRATION DEPTH DETECTOR AND DEVICE FOR MONITORING RESPIRATORY ACTIVITY EMPLOYING SAME

BACKGROUND OF THE INVENTION

1. Field of the Invention

The present invention relates to a device for determining the respiration rate and/or respiration depth of a patient (i.e., the physical exertions being made in an effort to breathe), having a sensor for sensing heart sounds, and to an apparatus for monitoring the respiration of a patient, including such a device.

2. Description of the Prior Art

Sleep apnea is a rather common disorder with diffuse symptoms. Usually during daytime the patient experiences fatigue, concentration problems and problems of staying awake. During night the patient's sleep is disrupted by episodes of apnea, usually caused by the epiglottis falling back and obstructing the airways. The apnea causes the person to awake thus disrupting the normal sleep pattern.

Monitoring of the respiration of a patient is needed for several purposes. Sudden infant death syndrome (SIDS) is, for example, one of the most common causes of death among infants under the age of one year. During the night infants normally experience apnea. A healthy infant will awake so as to resume breathing if the apnea lasts too long. If the infant is unable to awake itself, however, accidental suffocation and sudden death can occur. The reason for the inability of some infants to awaken themselves and the etiology of SIDS is to a large extent unknown but some correlation to rotavirus infection has been found. The clinical manifestation consists, as mentioned, in interruptions of the breathing of the infant during sleep and as a consequence death of the infant.

The usual way of investigating apnea is to monitor respiration and blood oxygen saturation during sleep. The respiration signal will indicate the episodes of apnea, while the blood oxygen signal indicates severity of the apnea.

Several respiration monitoring systems are known. Thus in e.g. U.S. Pat. No. 5,143,078 a monitoring system is described to determine a patient's respiration rate from breath sounds by an appropriate sensor, like a microphone. Special means are provided for reducing the effects of heart sounds and ambient noise.

An infant health monitoring system is disclosed in U.S. Pat. No. 5,479,932 in which, in addition to respiration of the infant, also large motor movement and heart beats are detected simultaneously and an alarm signal is generated only when anomalies are found in all three above-mentioned health related conditions. In this way false alarms are eliminated.

A sudden infant death syndrome monitor and stimulator is described in U.S. Pat. No. 5,515,865. Movements and acoustic activity, e.g. heartbeats and breathing, are then detected and a stimulator, which stimulates movement activity or acoustic activity by the infant, is operated when no movement activity and no acoustic activity are detected.

In U.S. Pat. No. 5,105,354 a method and apparatus are disclosed for forecasting sudden infant death syndrome by utilizing a characteristic change in the correlation between respiration and heart beats of infants, which occurs a few minutes before the start of a sleep-apnea episode.

European Application 0 504 945 discloses an apparatus for diagnosing and quantitatively analyzing apnea by recording the heart rate using ECG electrodes, respiration and snoring sounds detected by a microphone, the blood oxygen saturation degree by an oximeter and the position of the patient monitored by a suitable position sensor. The recorded data are transferred to a computer for further analysis.

A more recent way of determining the respiration rate and to some degree the respiration depth of a patient has been proposed which is based on the fact that the amplitude of heart sounds varies in a characteristic manner during the respiration cycle. One reason for this phenomenon is that the respiration changes the geometry of the chest, which means that the mechanical coupling between the heart and the sensor is changed, which in its turn changes the amplitude of the heart sounds picked up by the sensor. Another reason is that the filling of the heart with blood is dependent on the pressure in the thorax, and respiration influences this pressure. The filling of the heart, in turn, influences the strength of the heart beats and this strength affects the amplitude of the heart sounds.

SUMMARY OF THE INVENTION

An object of the present invention is to provide a simple and reliable device for determining the respiration rate and to some degree the respiration depth of a patient by utilizing the amplitude variation of heart sounds.

This object is achieved, according to the invention, in a device having a sensor for sensing heart sounds, and by an analyzer for analyzing the variation of the amplitude of the sensed heart sounds to determine the respiration rate and respiration depth from this amplitude variation.

Another object of the invention is to provide an apparatus for monitoring the respiration of a patient including such a device as described immediately above.

This object is achieved, according to the invention, in a respiration monitoring apparatus which is having an analyzer arranged to determine a first anomaly in the amplitude variation as an indication of a respiration anomaly.

According to another embodiment of the apparatus of the invention, a second sensor is provided for measuring the degree of blood oxygen saturation. This second sensor supplies a signal to the analyzer for analysis together with sensed heart sound data. Additionally, a body movement sensor can be provided to sense body movements of the patient for supplying sensed body movement data to the analyzer for analysis together with other sensed data. By adding these additional data to the sensed heart sound data a more reliable and thorough investigation or diagnosis of the respiration can be made.

In another embodiment of the apparatus, the analyzer triggers a first alarm in response to the determination of a respiration anomaly giving nursing staff or parents of an infant a possibility to intervene. Just waking the patient may often be enough for the patient to regain breathing.

In another embodiment of the apparatus of the invention, the analyzer is arranged to determine a second anomaly in the amplitude variation of the sensed heart sounds as an indication of an anomaly other than the respiration anomaly. This other anomaly can be, e.g., no heart sounds being detected, which probably is due to a dislocation of the sensor. It is thus possible to monitor also the correct functioning of the apparatus. The analyzer is then preferably arranged to trigger a second alarm in response to the determination of this other anomaly. The first and second alarms can suitably be realized by an alarm unit controlled by the analyzer to deliver acoustic and/or visual signals and/or mechanical vibration signals of two different qualities (e.g., different types of intensities).

In another embodiment of the apparatus according to the invention, the sensor is an accelerometer, disposed to detect heart sounds. The accelerometer is preferably a piezoelectric element with an amplifier and a signal pre-conditioning circuit. The signal pre-conditioning circuit can include high-pass filtering, rectifying and a signal smoothing stage. By choosing the cut-off frequency of the high-pass filter to about 100 Hz, frequencies originating from body movements of the patient, normally in the range of 1–5 Hz, are removed, thus making the functioning of the apparatus reliable also when the patient is moving.

According to another embodiment of the apparatus of the invention, the sensor and the analyzer are mounted in a pacemaker. In this way a rate responsive pacemaker, based on respiration, is obtained.

In another embodiment of the apparatus according to the invention the heart sound sensor, the analyzer and an electric supply are located in a common housing having a replaceable sticky surface layer for attachment to the skin of the patient's chest. The housing can have the shape of a disc with a diameter of about 30 mm and a thickness of a few mm. It allows for change of battery and can be carried by the patient without any discomfort.

In another embodiment of the apparatus according to the invention, the heart sound sensor is contained in a recording device also having a memory for storing sensed heart sound data for subsequent transfer to the analyzer, which is separated from the device. The recording device has a sticky surface layer for attachment to the skin of the patient's chest. A blood oxygen saturation sensor and/or a body movement sensor can be connected to the memory for transmission of measured data via a radio frequency, optical or wire communication link. The analyzer has a data processing unit, such as a computer, and is designed as a stationary unit intended to be placed in a hospital. In this way all recordings of data could be performed by the patient at home, in contrast to the investigation possibilities for e.g. sleep apnea associated with known techniques, which require a one-night stay at a hospital, which is a costly procedure. Furthermore such conventional equipment is bulky and often interferes with the patient under investigation, thus giving an unreliable diagnosis. The above-mentioned embodiments of the apparatus according to the invention are small units which will interfere minimally with the normal sleep of the patient, can be manufactured at a relatively low cost, and allow existing personal computers to be used for the analysis. The recording device carried by the patient even can be designed so as to be able to be directly plugged into an ordinary PCMCIA input adapter of personal computers for transfer of data stored in the memory of the recording device to the computer for analysis.

DESCRIPTION OF THE DRAWINGS

FIGS. 1a, 1b and 1c and 2a and 2b are diagrams illustrating the relation between 15 sensed heart signals and respiration.

FIG. 3 shows a pacemaker having a sensor with associated electronics used in the device and apparatus according to the invention.

FIG. 4 shows the sensor of FIG. 3 more in detail.

DESCRIPTION OF THE PREFERRED EMBODIMENTS

FIG. 1a shows heart sound activity, picked up by an accelerometer and amplified. FIG. 1b shows a surface ECG. FIG. 1c shows the left ventricular pressure respectively, as functions of the same time line. The opening and closing of the aortic valve can be clearly observed in the accelerometer signal and are indicated in the corresponding curve. From FIGS. 1a, 1b and 1c, it appears that the amplitude of the heart sounds varies with the respiration. This appears still more clearly from FIGS. 2a and 2b.

FIGS. 2a shows the accelerometer signal after high-pass filtering (the cut-off frequency being 100 Hz), rectifying and smoothing. FIG. 2b shows the signal out of a respirator for determining the respiration in this case. As appears from these diagrams, the respiration frequency is very well reproduced in the sensed heart sound signal. A very close correlation between the mechanical heart activity and the respiration and the respiration rate thus can be directly extracted from the heart sound curve.

As mentioned above the invention can be used in a pacemaker to provide a rate responsive pacemaker, based on the respiration of the patient. FIG. 3 shows such a pacemaker 2 with an accelerometer 4 mounted inside the pacemaker can.

Figure 5:
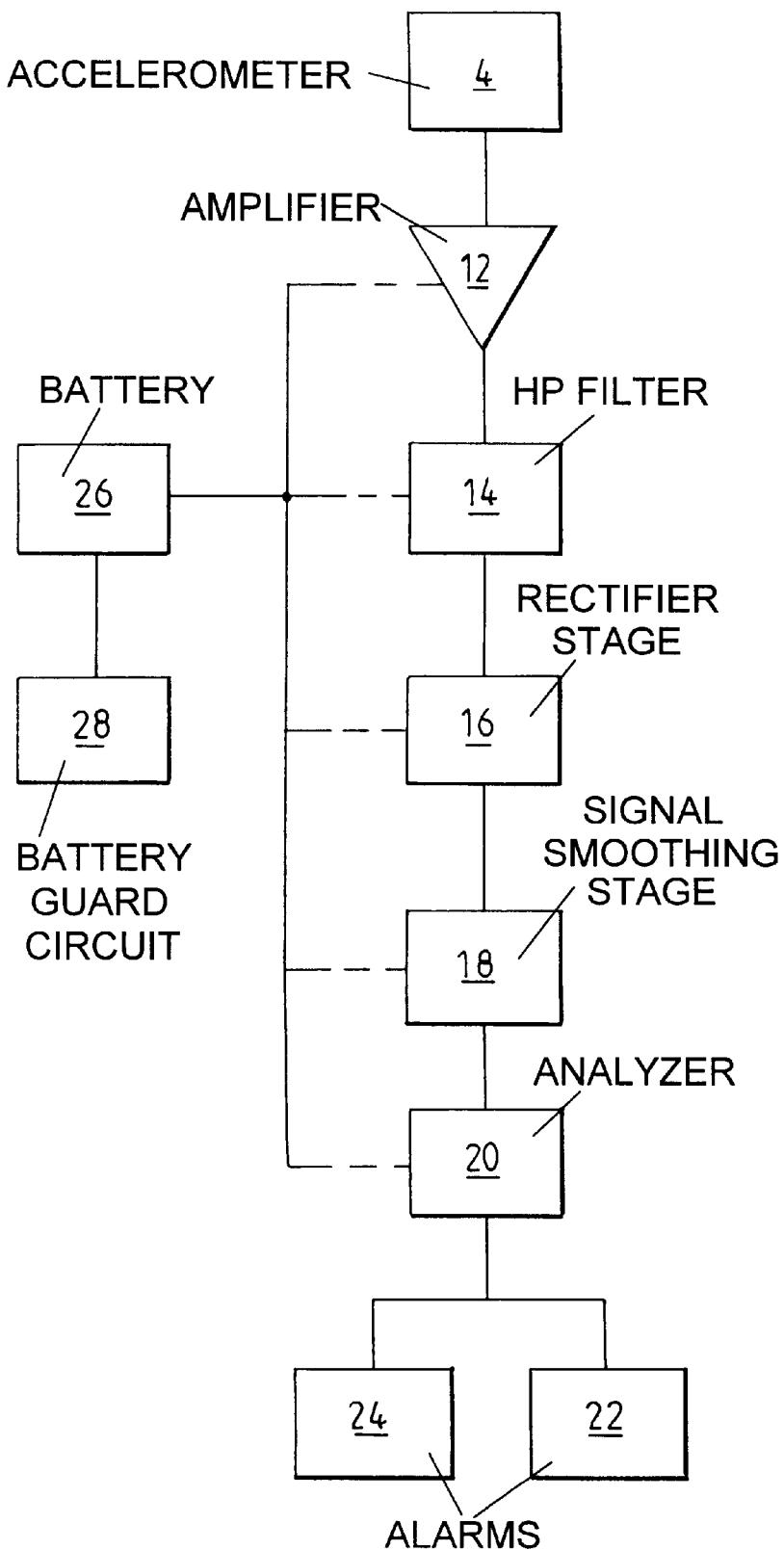
FIG. 5 shows a block diagram of an embodiment of the apparatus according to the invention.

The accelerometer 4, which is shown more in detail in FIG. 4, is of a piezoelectric type. The accelerometer 4 has an L-shaped piezoelectric rod 6 having a weight 8 fixed at a free end of the rod 6. The other end of the rod 6 is attached to a printed circuit board 10 having the associated electronics. The electronics include a non-inverting amplifier 12 with a lower cut-off frequency of about 20 Hz and a gain of 2000, a high-pass filter 14, a rectifier stage 16, a signal smoothing stage 18 and an analyzer 20 (see FIG. 5). Thus the signal from the piezoelectric element 6 is first amplified and then high-pass filtered. The cut-off frequency of the high-pass filter 14 is selected to be to 100 Hz. Frequencies related to body movements of the patient are thus removed from the sensed signal which makes the device and the apparatus function reliably even when carried by a patient in motion. The analyzer 20 is a data processor, like a computer.

If normal variation is detected in the amplitude of the sensed heart sound signal the apparatus gives an "OK" audio signal. If heart sounds with an amplitude variation which is too low are detected and last beyond a period of time of predetermined length of time, a first alarm 22, preferably a high intensity audio buzzer, is triggered to indicate an apnea episode. If no heart sounds are sensed during a predetermined time, a second alarm 24 is triggered to indicate a failure, probably due to dislodgement of the sensor. These two alarms are preferably realized by a single alarm unit which delivers acoustic and/or visual signals and/or mechanical vibration signals of two different qualities.

The necessary electric supply to the electronics is delivered by a battery 26 provided with a low battery guard circuit 28.

The device according to the invention can be mounted inside a 10 pacemaker can as described above. It can, however, also be mounted in a housing intend to be attached to the skin of the patient's chest. The device is then disc-shaped with a diameter of 30 mm and a thickness of a few mm. To allow for change of battery the housing has a replaceable, preferably sticky surface layer for attachment to the skin.

Figure 6:
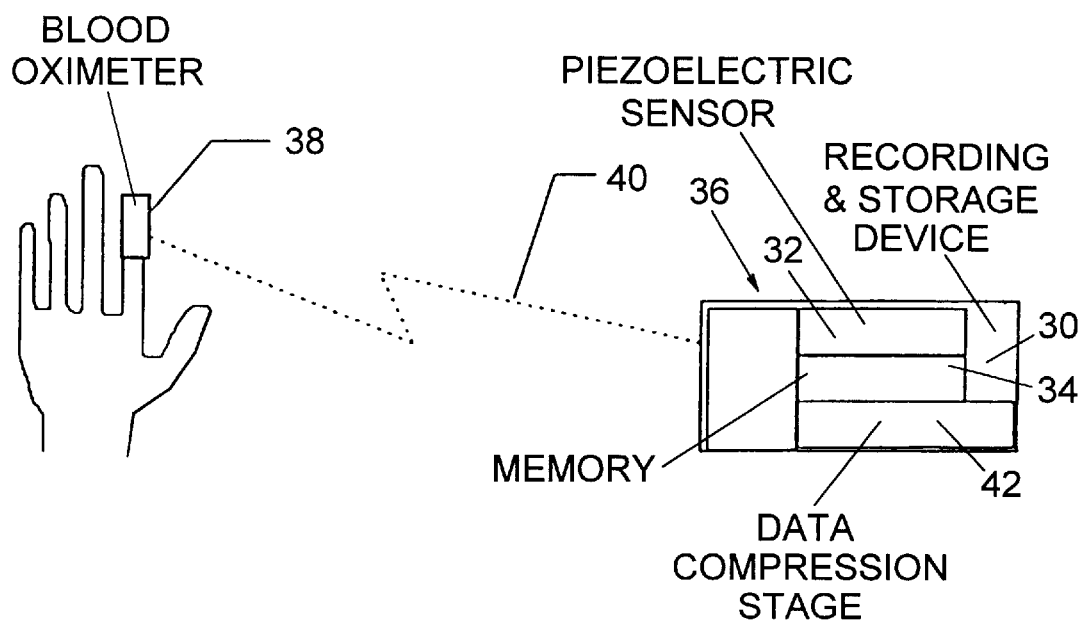
FIG. 6 shows an embodiment of the invention in which the analyzer is separated from the recording and storing device.

FIG. 6 shows an embodiment with a recording and storage device 30 having a heart sound sensor in the form of a piezoelectric sensor 32, and a memory 34 for storing sensed data. The device 30 is intended to be attached to the skin of the chest wall of the patient by a sticky pad, at the side 36, with the piezoelectric sensor 32 adjacent to the chest wall.

A second sensor in the form of a finger worn oxygen sensor (oximeter) 38 attachable to the finger of a patient to continuously measure the degree of blood oxygen saturation. This sensor 38 is suitably a light emitting oxygen measuring sensor and this sensor is connected to the memory 34 of the device 30 via a radio frequency telemetry link or an optical or wire communication link, indicated at 40.

In addition, data from a body movement sensor (not shown in FIG. 6), can also be supplied to the memory 34.

After the data collection or recording phase, which is suitably performed by the patient at home, the device 30 is sent, e.g. by mail, to a hospital, where an analyzer is available. The data stored in the memory means 34 is then transferred to the computer of the analyzer. For that purpose the device 30 can be designed for being directly plugged into an ordinary PCMCIA adapter of the computer.

The device 30 preferably has a data compression stage 42 for facilitating storage, transfer and even analysis of large volumes of data.

By simultaneous recording of respiration information by heart sound sensing, degree of blood oxygen saturation and body movements for analysis, more accurate assessment and reliable diagnosis of respiration disorders are obtained.

Although modifications and changes may be suggested by those skilled in the art, it is the intention of the inventors to embody within the patent warranted hereon all changes and modifications as reasonably and properly come within the scope of their contribution to the art.

We claim as our invention:

1. A respiration detector comprising:

a sensor which senses heart sounds emanating from a patient and for generating an electrical signal containing a signal component produced by said heart sounds, said signal component having a varying amplitude; and analyzer means, supplied with said electrical signal, for extracting said signal component and for analyzing variations of said amplitude of said signal component for identifying at least one of a respiration rate and a respiration depth from the variations of said amplitude.

2. A respiration detector as claimed in claim 1 further comprising means for producing an amplitude variation curve representing variations of the amplitude of said electrical signal and for identifying a predetermined portion of said amplitude variation curve, and for identifying if said predetermined portion exceeds a predetermined threshold value.

3. A respiration detector as claimed in claim 1 further comprising:

means for pacing a subject by supplying electrical stimulation pulses to said subject;

means for controlling said means for pacing dependent on said at least one of said respiration rate and respiration depth identified by said analyzer means; and a pacemaker housing containing said sensor, said analyzer means, said means for pacing and said means for controlling.

4. An apparatus for monitoring respiration of a subject, comprising:

a sensor which senses heart sounds emanating from a patient and for generating an electrical signal containing a signal component produced by said heart sounds, said signal component having a varying amplitude; and analyzer means, supplied with said electrical signal, extracting said signal component and for identifying an anomaly in variations of said amplitude of said signal component as an indication of a respiration anomaly.

5. An apparatus as claimed in claim 4 further comprising means for producing an amplitude variation curve representing variations of the amplitude of said electrical signal and for identifying a predetermined portion of said amplitude variation curve, and for identifying if said predetermined portion exceeds a predetermined threshold value.

6. An apparatus as claimed in claim 4 further comprising:

means for pacing a subject by supplying electrical stimulation pulses to said subject;

means for controlling said means for pacing dependent on said at least one of said respiration rate and respiration depth identified by said analyzer means; and a pacemaker housing containing said sensor, said analyzer means, said means for pacing and said means for controlling.

7. An apparatus as claimed in claim 4 wherein said analyzer means comprises means for identifying a decrease below a predetermined limit of amplitude variation during a predetermined period of time as said respiration anomaly.

8. An apparatus as claimed in claim 7 wherein said analyzer comprises means for continuously comparing said amplitude with predetermined threshold values for detecting a decrease of variations of said amplitude below said predetermined limit.

9. An apparatus as claimed in claim 4 wherein said analyzer means comprises means for identifying a respiration rate from said variations of said amplitude of said electrical signal, and for identifying a respiration rate below a predetermined respiration rate as said respiration anomaly.

10. An apparatus as claimed in claim 4 wherein said sensor comprises a first sensor, and said apparatus further comprising a second sensor which measures a degree of blood oxygen saturation and generating a further electrical signal, and wherein said analyzer means is supplied with said further electrical signal together with said electrical signal and comprises means for identifying said respiration anomaly from a combination of said electrical signal and said further electrical signal.

11. An apparatus as claimed in claim 4 wherein said sensor comprises a first sensor, and said apparatus further comprising a second sensor which sensing body movements and generating a further electrical signal, and wherein said analyzer means is supplied with said further electrical signal together with said electrical signal and comprises means for identifying said respiration anomaly from a combination of said electrical signal and said further electrical signal.

12. An apparatus as claimed in claim 4 further comprising alarm means for emitting an alarm, and wherein said analyzer means comprises means for triggering said alarm means to emit said alarm upon identification of said respiration anomaly.

13. An apparatus as claimed in claim 4 wherein said respiration anomaly comprises a first anomaly, and wherein said analyzer means comprises means for identifying a second anomaly, other than said respiration anomaly, from said electrical signal.

14. An apparatus as claimed in claim 4 further comprising alarm means for emitting a first alarm and a second alarm, and wherein said analyzer means comprises means for triggering said alarm means to emit said first alarm upon identification of said first anomaly and for triggering said alarm means to emit said second alarm upon identification of said second anomaly.

15. An apparatus as claimed in claim 14 wherein said alarm means comprises means for emitting a first acoustic signal, having a first acoustic quality, as said first alarm and for emitting a second acoustic signal, having a second acoustic quality different from said first acoustic quality, as said second alarm.

16. An apparatus as claimed in claim 14 wherein said alarm means comprises means for emitting a first visual signal, having a first visual quality, as said first alarm and for emitting a second visual signal, having a second visual quality different from said first visual quality, as said second alarm.

17. An apparatus as claimed in claim 14 wherein said alarm means comprises means for emitting a first mechanical signal, having a first mechanical quality, as said first alarm and for emitting a second mechanical signal, having a second mechanical quality different from said first mechanical quality, as said second alarm.

18. An apparatus as claimed in claim 4 wherein said sensor comprises an accelerometer.

19. An apparatus as claimed in claim 18 wherein said accelerometer comprises a piezoelectric element having an output connected to an amplifier which emits an amplified signal, and signal pre-conditioning means, supplied with said amplified signal, for pre-conditioning said amplified signal to produce a pre-conditioned signal comprising said electrical signal.

20. An apparatus as claimed in claim 4 further comprising an electrical supply connected to said sensor and to said analyzer means, and a housing containing said sensor, said analyzer means and said electrical supply, and replaceable means for extracorporeally cutaneously adhering said housing at a location on a patient adapted for detecting said heart sounds.

21. An apparatus as claimed in claim 20 wherein said electric supply comprises a battery with a battery guard circuit.

22. An apparatus as claimed in claim 4 further comprising:
    recording means, containing said sensor and disposed remote from said analyzer means, for recording and storing said heart sounds as recorded data in a memory for subsequent transfer to said analyzing means, said recording means having a housing and replaceable means for extracorporeally cutaneously adhering said housing at a location on a subject adapted for recording said heart sounds.

23. An apparatus as claimed in claim 22 further comprising a blood oxygen saturation sensor which produces measured blood oxygen saturation data, and means for communicating said measured blood oxygen saturation data from said blood oxygen saturation sensor to said memory in said recording means for storing said measured blood oxygen saturation data in said memory together with said recorded data for subsequent transfer to said analyzer means.

24. An apparatus as claimed in claim 23 wherein said means for communicating comprises a communication link selected from the group consisting of a radio-frequency communication link, an optical communication link and a wired communication link.

25. An apparatus as claimed in claim 22 further comprising a body movement sensor which generates body movement data, and means for supplying said body movement data from said body movement sensor to said memory in said recording means for storage in said memory together with said recorded data for subsequent supply to said analyzer means.

26. An apparatus as claimed in claim 22 wherein said recording means includes data compression means for compressing said recorded data stored in said memory.

27. An apparatus as claimed in claim 22 wherein said analyzer means comprises a stationary data processing unit.

* * * * *